United States Patent
Blasius

(10) Patent No.: US 11,911,244 B2
(45) Date of Patent: Feb. 27, 2024

(54) ABSORBENT ARTICLE

(71) Applicant: Better Made Hemp, LLC, Northville, MI (US)

(72) Inventor: Alexandra Blasius, Northville, MI (US)

(73) Assignee: Better Made Hemp, LLC, Northville, MI (US)

(*) Notice: Subject to any disclaimer, the term of this patent is extended or adjusted under 35 U.S.C. 154(b) by 768 days.

(21) Appl. No.: 16/994,143

(22) Filed: Aug. 14, 2020

(65) Prior Publication Data

US 2021/0045933 A1 Feb. 18, 2021

Related U.S. Application Data

(60) Provisional application No. 62/887,087, filed on Aug. 15, 2019.

(51) Int. Cl.
*A61F 13/20* (2006.01)
*A61F 13/34* (2006.01)

(52) U.S. Cl.
CPC ........ *A61F 13/208* (2013.01); *A61F 13/2028* (2013.01); *A61F 13/2068* (2013.01);
(Continued)

(58) Field of Classification Search
CPC ................ A61F 13/208; A61F 13/2028; A61F 13/2068; A61F 13/2071; A61F 13/2074; A61F 13/34
See application file for complete search history.

(56) References Cited

U.S. PATENT DOCUMENTS 2,306,406 A * 12/1942 Robinson ............ A61F 13/2068
604/377
4,212,301 A 7/1980 Johnson
(Continued)

FOREIGN PATENT DOCUMENTS

CN 109589443 A * 4/2019 .......... A61F 13/202
KR 20100101550 A * 9/2010 ......... A61F 13/2028

OTHER PUBLICATIONS

Glad Rags—Eco-Friendly Menstrual Products, https://gladrags.com/, downloaded Feb. 24, 2021, 8 pages.
(Continued)

*Primary Examiner* — Susan S Su
(74) *Attorney, Agent, or Firm* — Ina Agaj; Dickinson Wright PLLC

(57) ABSTRACT

An absorbent article includes a body portion extending along a first axis and having a proximal end and a distal end spaced from the proximal end along the first axis. The absorbent article also includes a plurality of layers radially disposed about the body portion. Each layer includes one or more absorbent petals each extending along a petal axis. The petal axis of one of the petals of one of the layers is angularly offset to the petal axis of an adjacent petal of an adjacent layer. The one or more absorbent petals are movable between a compacted configuration and an expanded configuration. The one or more absorbent petals, when introduced to a fluid, is configured to absorb the fluid and transition from the compacted configuration to the expanded configuration. The absorbent article includes a string coupled to the body portion. The body portion and/or string includes hemp.

22 Claims, 6 Drawing Sheets

(52) U.S. Cl.
CPC ...... *A61F 13/2071* (2013.01); *A61F 13/2074* (2013.01); *A61F 13/34* (2013.01)

(56) References Cited

U.S. PATENT DOCUMENTS

| | | | |
|---|---|---|---|
| 5,112,348 A * | 5/1992 | Glassman | A61F 13/34 604/385.18 |
| 6,558,362 B1 | 5/2003 | Chaffringeon | |
| 6,747,184 B2 | 6/2004 | Zadini et al. | |
| 7,112,192 B2 | 9/2006 | Hasse et al. | |
| 7,214,218 B2 | 5/2007 | Carlin | |
| 7,618,403 B2 | 11/2009 | Carasso et al. | |
| 8,057,453 B2 | 11/2011 | Chase et al. | |
| 8,827,974 B2 | 9/2014 | Schmidt-Forst | |
| 9,035,126 B2 | 5/2015 | Carasso et al. | |
| 9,107,775 B2 | 8/2015 | Edgett et al. | |
| 9,393,160 B2 | 7/2016 | McDaniel et al. | |
| 2002/0156442 A1 * | 10/2002 | Jackson | A61F 13/2068 604/385.18 |
| 2004/0043071 A1 * | 3/2004 | Pauletti | A61F 13/2074 424/484 |
| 2005/0096619 A1 | 5/2005 | Costa | |
| 2005/0277904 A1 | 12/2005 | Chase et al. | |
| 2007/0255232 A1 | 11/2007 | Chaffringeon | |
| 2007/0293836 A1 | 12/2007 | Hasse et al. | |
| 2008/0154174 A1 * | 6/2008 | Costa | A61F 13/2068 604/11 |
| 2009/0281514 A1 | 11/2009 | Glaug et al. | |
| 2013/0165893 A1 * | 6/2013 | Chase | A61F 13/2065 604/385.17 |
| 2017/0181899 A1 * | 6/2017 | Glaug | B29C 65/08 |
| 2021/0045943 A1 | 2/2021 | Blasius | |

OTHER PUBLICATIONS

House of Kells—Willowpads, http://thewillowstore.com/product-category/everyday-willow/natural-feminine-care/, downloaded Feb. 24, 2021, 1 page.

Honest—Organic Cotton Tampons, https://www.honest.com/personal-care-products/organic-cotton-tampons-no-applicator/cotton-tampons.html, downloaded Mar. 12, 2021, 3 pages.

* cited by examiner

ABSORBENT ARTICLE

CROSS-REFERENCE TO RELATED APPLICATIONS

This application claims priority to and all the advantages of U.S. Provisional Application 62/887,087 filed on Aug. 15, 2019, the entire content of which is incorporated herein by reference in its entirety.

BACKGROUND

Conventional absorbent articles are used to absorb and hold bodily exudates (e.g., urine, menses) and/or fluids. There are many different types of absorbent articles, which may include diapers, pants, sanitary napkins, and tampons, for example. Some absorbent articles are inserted inside a body of a wearer, particularly tampons, to prevent leakage of bodily exudates. During a menstrual cycle, a wearer may insert a tampon and leave the tampon inside the body for hours at a time to absorb and hold the bodily exudates. It is often desirable to prevent any leakage during use and, at the same time, prevent any bacterial buildup that could potentially harm the wearer.

During the menstrual cycle, blood is a major reason for germs to grow, which causes unpleasant odor and raises the possibility of bacterial buildup. Some absorbent articles include multiple layers that are capable of quickly absorbing fluids and subsequently passing the fluids to the next layer to retain the fluids. With multiple layers, the blood is spread out between the layers such that germs are less likely to grow and build up. By having an absorbent article positioned inside the body for a certain amount of time, it is desirable that the absorbent article is made of material and layers that do not compromise the health of the wearer.

Most women experience painful symptoms or discomfort leading up to, during, and after menstruation. For some, symptoms are so severe that it becomes difficult to carry out normal tasks of daily life. Symptoms may include muscle aches, headaches, joint pain, bloating, acne, abdominal cramps, constipation, tenderness, lower back pain, and fatigue. Conventional absorbent articles may lack efficient composition to alleviate any of the aforementioned symptoms.

Leakage may occur due to the less than optimal fit of conventional absorbent articles. Because of the layers' many properties, such as absorbency, flexibility, and structure, it may be desirable to incorporate a more efficient structure into such articles to prevent any bacterial buildup and, at the same time, prevent any leakage. Finally, absorbent articles are a single use product. Once the absorbent article is used, the wearer throws the absorbent article away. In such instances, the absorbent article may not be easily degradable or environmentally friendly. In other instances, the absorbent article may not be made from renewable resources.

Accordingly, there is a need for an improved absorbent article.

SUMMARY OF THE INVENTION AND ADVANTAGES

An absorbent article includes a body portion extending along a first axis and having a proximal end and a distal end spaced from the proximal end along the first axis. The absorbent article also includes a plurality of layers radially disposed about the body portion. Each layer includes one or more absorbent petals each extending along a petal axis. The petal axis of one of the petals of one of the layers is angularly offset to the petal axis of an adjacent petal of an adjacent layer. The one or more absorbent petals are movable between a compacted configuration and an expanded configuration. The one or more absorbent petals, when introduced to a fluid, is configured to absorb the fluid and transition from the compacted configuration to the expanded configuration. The absorbent article includes a string coupled to the body portion. The body portion and/or string includes hemp.

Accordingly, the absorbent article having the body portion and/or the string comprising hemp is environmentally friendly and alleviates menstruation symptoms.

BRIEF DESCRIPTION OF THE DRAWINGS

Referring now to the drawings, exemplary illustrations are shown in detail. Although the drawings represent schematic configurations, the drawings are not necessarily to scale and certain features may be exaggerated to better illustrate and explain an innovative aspect of an illustrative configuration. Further, the exemplary illustrations described herein are not intended to be exhaustive or otherwise limiting or restricting to the precise form and configuration shown in the drawings and disclosed in the following detailed description.

Advantages of the present disclosure will be readily appreciated, as the same becomes better understood by reference to the following detailed description when considered in connection with the accompanying drawings.

DETAILED DESCRIPTION

Figure 1:
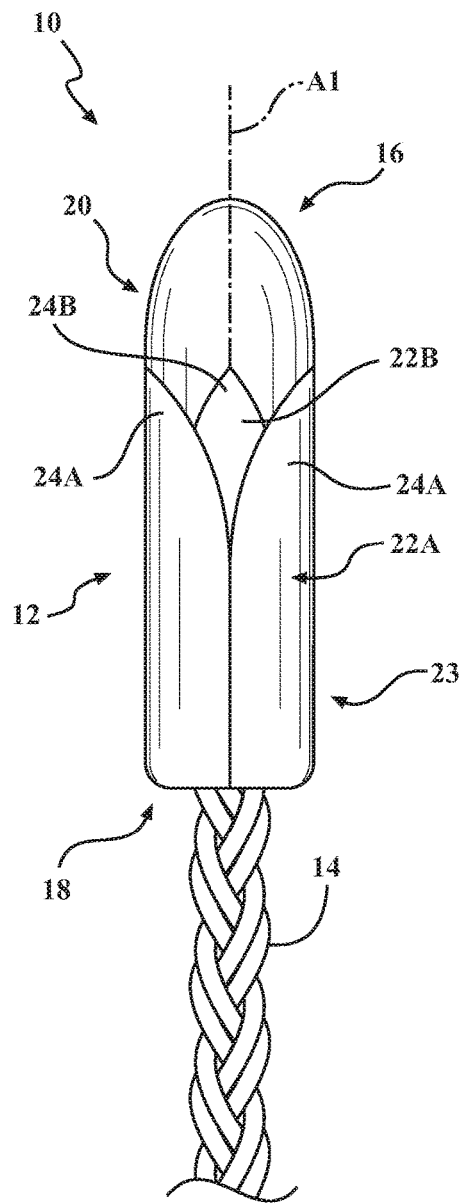
FIG. 1 is a side perspective view of an absorbent article including an absorbent pledget including a plurality of layers and petal ends in a compacted configuration.

An absorbent article 10 is shown in FIGS. 1-6. The absorbent article 10, which commonly may be referred to as a tampon, may be inserted by a wearer during menstruation. With reference to FIG. 1, the absorbent article 10 includes a body portion 20 extending along a first axis A1 and having a proximal end 16 and a distal end 18 spaced from the proximal end 16 along the first axis A1. The absorbent article 10 also includes a plurality of layers 22 radially disposed about the body portion 20. Each layer 22 includes one or more absorbent petals 23 each extending along a petal axis P1. The petal axis P1 of one of the petals 23 of one of the layers is angularly offset to the petal axis of an adjacent petal of an adjacent layer. The one or more absorbent petals 23 are movable between a compacted configuration and an expanded configuration. The one or more absorbent petals 23, when introduced to a fluid, is configured to absorb the fluid and transition from the compacted configuration to the expanded configuration. The absorbent article 10 includes a string 14 coupled to the body portion 20. The body portion 20 and/or string 14 includes hemp.

The absorbent article 10 further includes an absorbent pledget 12. In various configurations, the absorbent pledget 12 is the body portion 20. In other configurations, the absorbent pledget 12 includes the body portion 20. It will be appreciated that the absorbent pledget 12 may be interchangeably the body portion 20.

The plurality of layers 22 each includes one or more absorbent petals 23 each extending along a petal axis P1 and having a petal end 24. The petal axis P1 of one of the petals of the layers 22 is angularly offset to the petal axis P2 of an adjacent petal of an adjacent layer with respect to the first axis A1. The one or more absorbent petals are movable between a compacted configuration, where each of the plurality of layers 22 form a generally cylindrical shape and each of the petal ends 24 generally point towards the proximal end 16 of the body portion 20, and an expanded configuration, where the petal ends of the one or more absorbent petals are radially spaced from the first axis A1 such that the petal axis A1 of at least one of the absorbent petals is angled with respect to the first axis A1. In the compacted configuration, the petal ends 24 are configured to be substantially parallel to the first axis A1. The plurality of layers will be discussed in further detail below.

Figure 3:
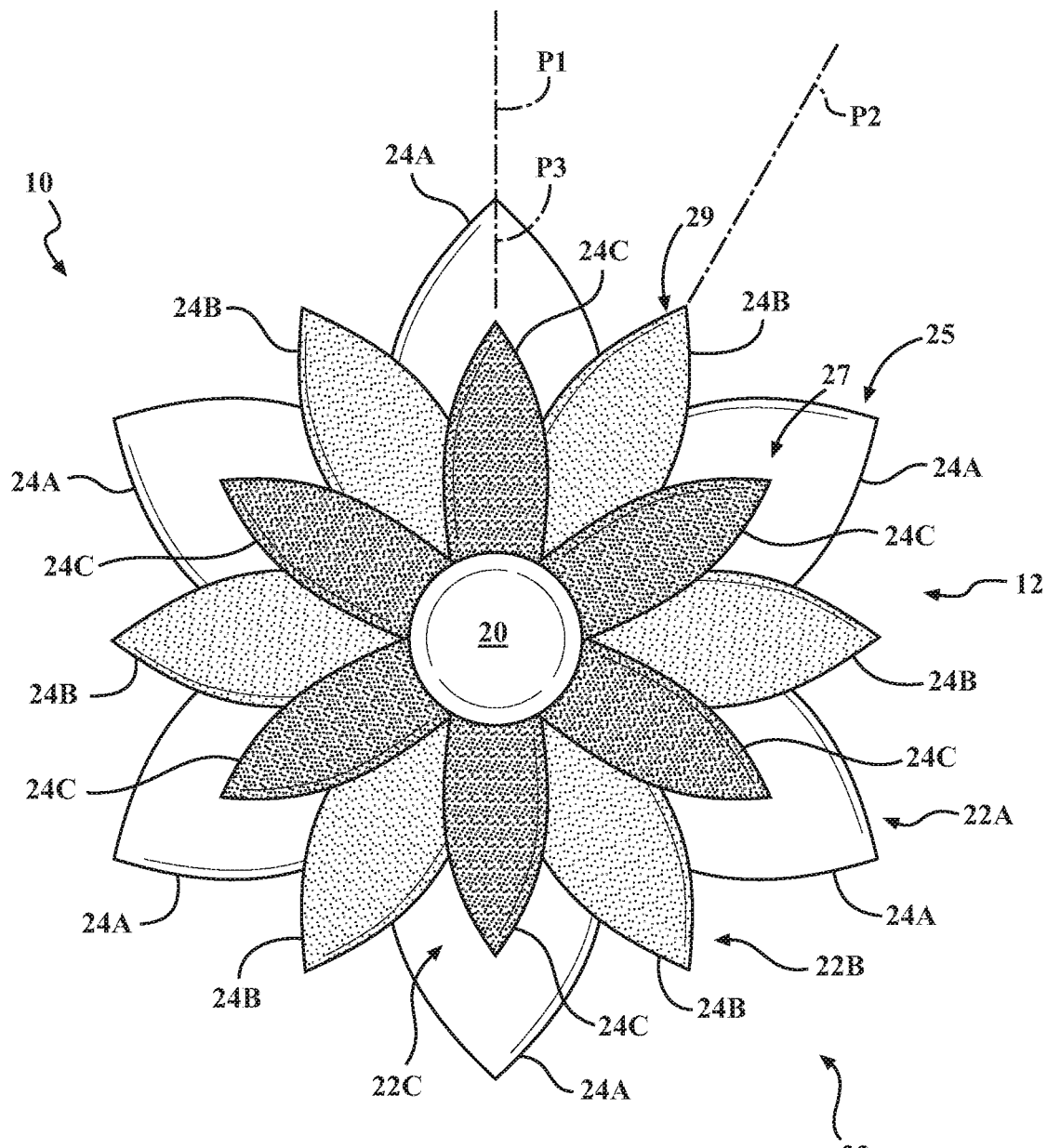
FIG. 3 is a top perspective view of the absorbent article of FIG. 2.
Figure 4:
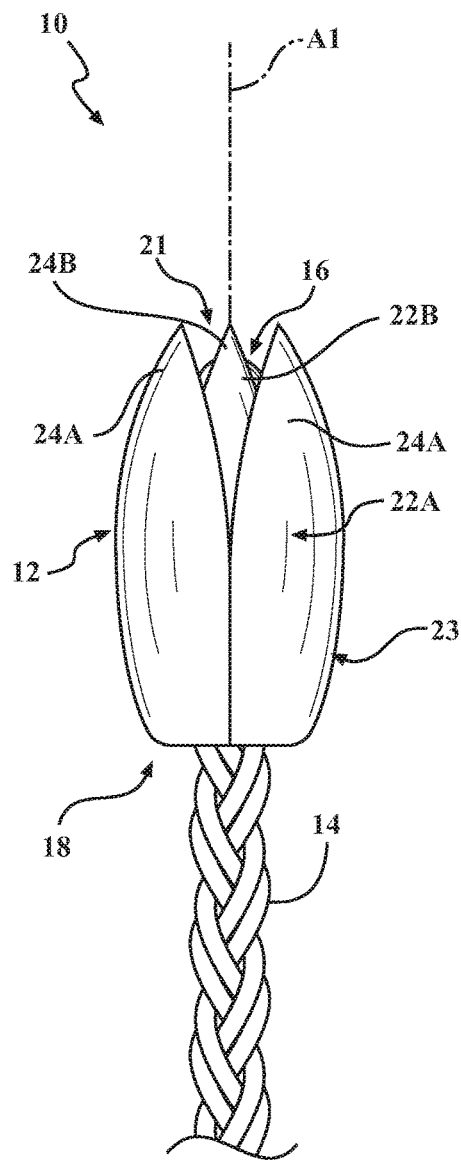
FIG. 4 is a side perspective view of another configuration of the absorbent article.
Figure 5:
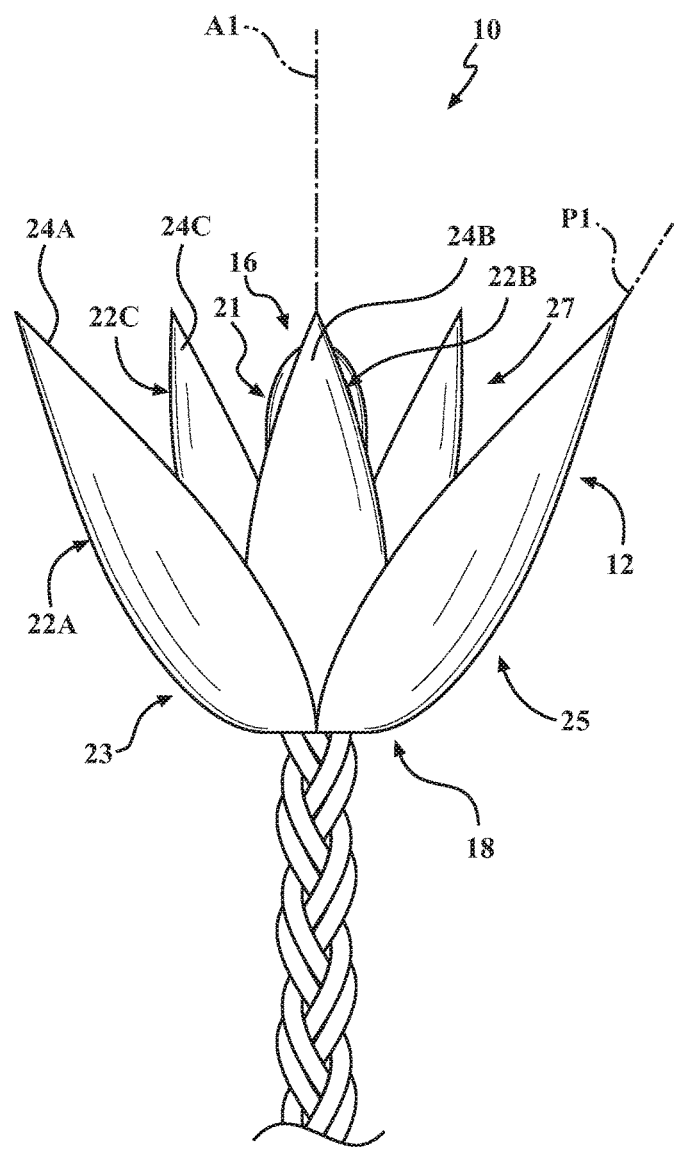
FIG. 5 is the absorbent article of FIG. 4 in an expanded configuration.

The one or more absorbent petals 23, when introduced to a fluid, is configured to absorb and transition from the compacted configuration (as illustrated in FIGS. 1 and 4) to the expanded configuration (as illustrated in FIGS. 3 and 5) for preventing fluid leakage. In one configuration, the absorbent article 10 includes a string 14 coupled to the distal end 18 of the body portion 20. In a preferred embodiment, the absorbent pledget 12 and/or the string 14 includes hemp.

When present, the string 14 is configured to aid the wearer in removal of the absorbent article 10 from the wearer's body. The proximal end 16 is adapted to be the leading end during insertion into the wearer's body and enters the wearer's body first. The distal end 18 is adapted to be the tailing end during insertion and enters the wearer's body last. After usage, the wearer, using one hand, may pull on the string 14 extending from the distal end 18 to remove the absorbent article 10 with the proximal end 16 exiting the wearer's body last.

Figure 2:
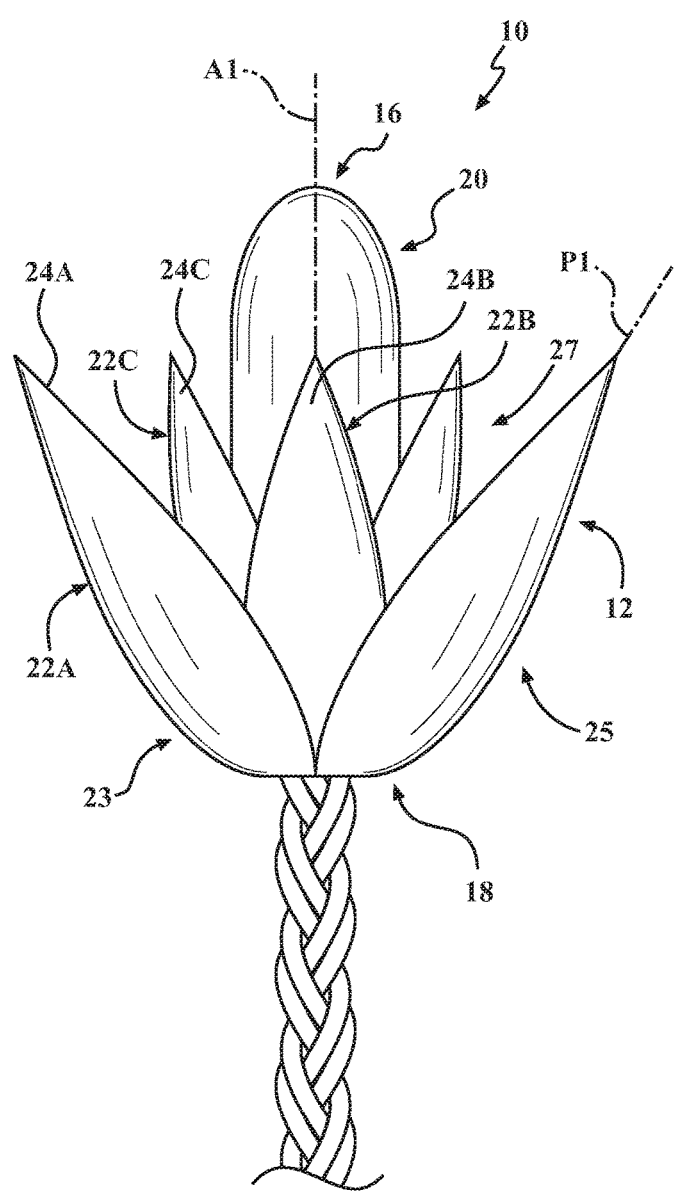
FIG. 2 is the absorbent article of FIG. 1 in an expanded configuration.

The string 14 may be configured to be a removal mechanism after use. The string 14 may be secured to the distal end using any method for attachment. The string 14 may take any form suitable to aid the wearer in removal including, but not limited to, braided, twisted, looped, tabbed, or the like. It is contemplated that the string 14 may include any number of strings. For example, as shown in FIGS. 1-2, the string 14 includes a set of two strings braided with another set of two strings. In another example, the string 14 may include one string twisted with a set of two strings. It is also contemplated that the string 14 may be formed of material characterized by a directional elasticity. For example, elasticity in the along the first axis A1 is larger than elasticity along an axis perpendicular to the first axis A1.

Figure 6:
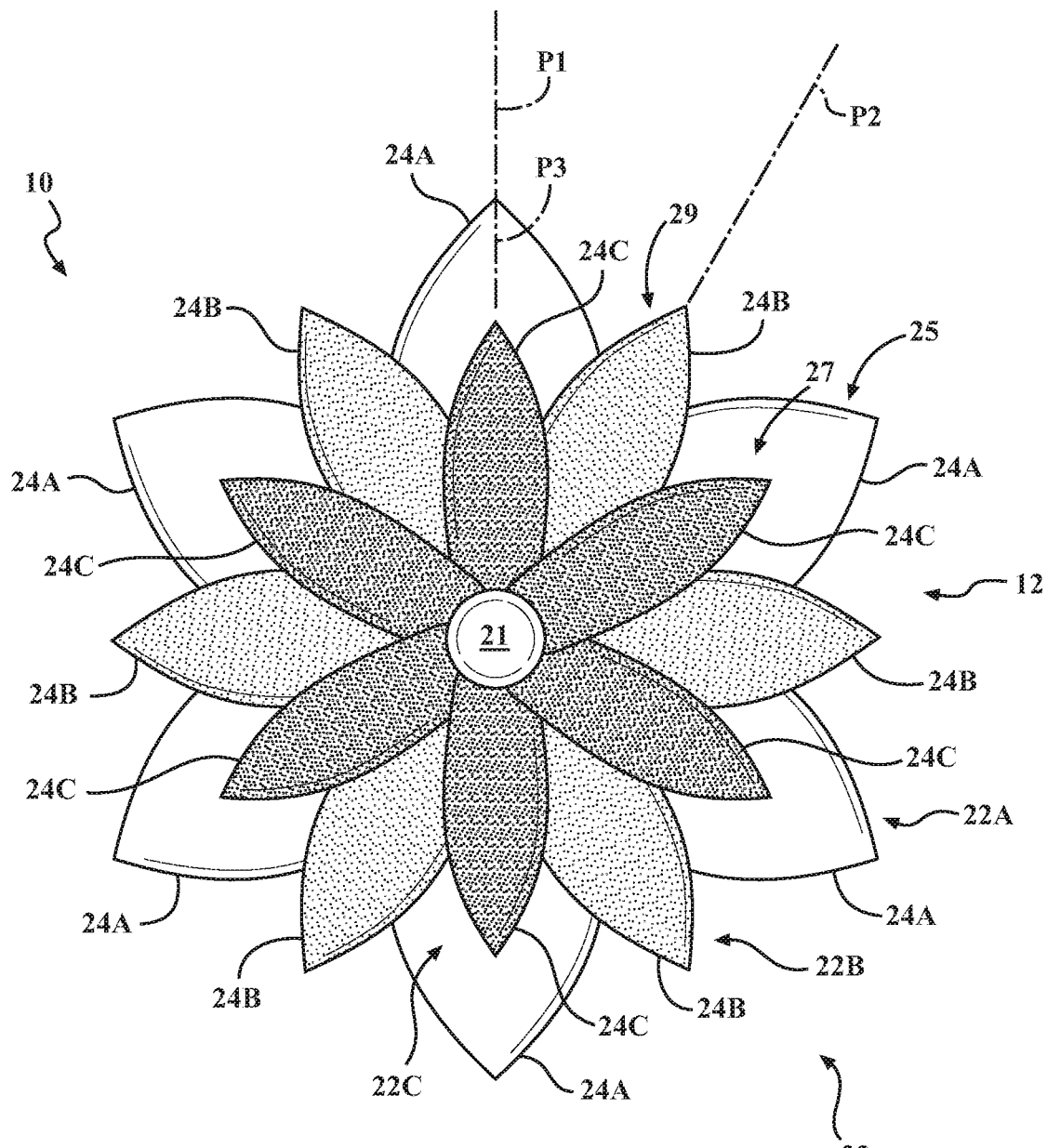
FIG. 6 is a top perspective view of the absorbent article of FIG. 5.

The plurality of layers 22 may enclose the body portion 20. FIGS. In one configuration, as shown in FIGS. 1-3, the body portion 20 may be substantially enclosed by a plurality of layers 22. In another configuration, as shown in FIGS. 4-6, the plurality of layers 22 may fully enclose a core 21. In these configurations, the body portion 20 may be the core 21. In yet another configuration, the plurality of layers 22 may enclose 50% or more of a length of the core. In yet another configuration, the plurality of layers 22 may enclose less than 50% a length of the core. It is contemplated that the core and/or the body portion may be formed by the plurality of layers 22.

The body portion 20 or core 21 may be made in various s and sizes. For example, as shown throughout the FIGS., the body portion 20 or core 21 extends along the first axis A1 and has a generally cylindrical. In another example, the core may be cone d with the distal end 18 being wider than the proximal end 16. It should be understood that the body portion 20 or core 21 may extend the entire length of the absorbent article 10.

The body portion 20 or core 21 may change shape and/or size during usage. For example, once inserted, the body portion 20 or core 21 may expand from its cylindrical shape and conform to contours of the wearer's body. As used herein, the term "core" refers to a material or combination of materials suitable for absorbing, distributing, collecting, and storing any type of bodily exudates. The shape and size of the body portion 20 or core 21 may be altered or convertible to meet any absorbent capacity requirements. Other shapes and sizes of the body portion 20 or core 21 are contemplated.

The plurality of layers 22 each includes one or more absorbent petals 23 having petal ends 24. The plurality of layers 22 is configured to aid in leakage prevention during use or when exposed to bodily fluids. The plurality of layers 22 and/or one or more absorbent petals 23 prevent substantial leakage during usage or when exposed to bodily fluids by absorbing fluids from the layer of the preceding one of the plurality of layers 22. Additional features and variations of the plurality of layers 22 and petal ends 24 will be described in greater detail below. It is to be appreciated that the term "fluids" may be interchangeable with "exudates," unless otherwise stated.

As shown in FIG. 1, a first layer 22A and a second layer 22B are shown. The first layer 22A includes two petal ends 24A, and the second layer 22B includes a petal end 24B. It will be appreciated that the absorbent article 10 may include any number of layers 22 (i.e. 22A, 22B, and so on) and each layer may include any number of petal ends 24 (i.e. 24A, 24B, and so on).

Referring to FIG. 2, the plurality of layers 22 includes an outer layer 25 disposed about the axis, and an inner layer 27 surrounded by the outer layer 25 such that the inner layer 27 is disposed between the outer layer 25 and the inner layer 27. When the body portion 20 is exposed to fluid, the outer layer 25 absorbs the fluid before the inner layer 27 such that the outer layer 25 moves from the compacted configuration to the expanded configuration before the inner layer 27. Further, in some configurations, the plurality of layers 22 includes an intermediate layer 29. The intermediate layer 29 is surrounded by the outer layer 25 with respect to the first axis A1 and surrounds the inner layer 27 with respect to the first axis A1, and wherein the petal axis of one of the petals of the outer layer 25 is angularly aligned with the petal axis of one of the petals of the inner layer 27. When the body portion 20 is exposed to fluid, the intermediate layer 29 absorbs the fluid before the inner layer 27 such that the intermediate layer 29 moves from the compacted configuration to the expanded configuration before the inner layer 27. It is contemplated that the plurality of layers may include any number of intermediate layers. For example, between the inner and outer layers, there may be three intermediate layers.

The plurality of layers 22 may vary in thickness. For example, thickness increases between the outer layer 25 to the inner layer 27. In this configuration, the inner layer 27 is thicker than the outer layer 25. In another example, the thickness decreases between the outer layer 25 to the inner layer 27. In this configuration, the outer layer 25 is thicker than the inner layer 27. In yet another example, the outer layer 25 may include two layers with one layer being thicker than the other layer. It is contemplated that any layers of the plurality of layers may also vary in thickness.

It is appreciated that the outer layer 25, inner layer 27, and/or the intermediate layer 29 may include a plurality of sub-layers. For example, the outer layer 25 may include six layers comprising hemp-fiber. In another example, the outer layer 25 may include two layers of hemp-fiber and the inner layer may include three layers of hemp-fiber. It is contemplated that the plurality of layers may comprise any number of layers and include various types of material.

In some configurations, the first layer 22A is the outer layer 25 and the second layer 22B is the inner layer 27. In other configurations, the first layer 22A is the outer layer and the second layer 22B is the intermediate layer 29, and a third layer 22C is the inner layer 27.

Alternatively, or additionally, the plurality of layers 22 may be intertwined with each other. For example, a portion of the inner layer 27 may be twisted with the outer layer 25. In another example, there are two intermediate layers between the outer and inner layers and the two intermediate layers are intertwined. The layers 22 may be intertwined in various methods. Methods may include, but are not limited to, coiling, twirling, lacing, braiding, linking.

The plurality of layers 22 may be formed from pieces of material having various shapes. For example, the plurality of layers 22 may be square-shaped. In yet another configuration, the plurality of layers may be triangle-shaped (See FIG. 9). Other geometric shapes are contemplated. In some configurations, the plurality of layers may be of different shapes. For example, an outer layer may be square-shaped and an inner layer is triangular-shaped.

One or more absorbent petals 23 are movable between the compacted configuration and the expanded configuration. Before usage or exposure to any bodily exudates, the plurality of layers 22, one or more absorbent petals 23, petal ends 24, or any combinations thereof are in the compacted configuration. In the compacted configuration, as shown in FIG. 1, each of the plurality of layers 22 and/or petal ends 24 form a generally cylindrical shape. For example, the plurality of layers 22 are folded from the center of each layer to surround the body portion 20. In another example, the plurality of layers 22 may each be attached around the body portion 20 or core 21. The layers 22 may be attached with an adhesive, via sewing, and other known attachment methods. In yet another example, the plurality of layers 22 may be radially disposed about the body portion 20 or core 21 and spaced along the first axis A1. It will be appreciated that the plurality of layers 22 may be radially disposed about the body portion 20 or core 21 in any direction. In yet another example, the plurality of layers 22 may each be wrapped around the body portion 20 or core 21. Other methods of forming the generally cylindrical shape with the plurality of layers 22 and/or petal ends 24 are contemplated.

One or more absorbent petals 23 may include a second end adjacent the body portion 20 and spaced from the petal end 24. In some configurations, the second end is configured to form a wider round portion that tapers toward the petal end 24. The petal end 24 may be configured to taper to a sharpened point, wherein the second end is wider than the petal end 24. In these configurations, the one or more absorbent petals 23 may form a teardrop shape. One or more absorbent petals 23 are configured to be formed with a degree of flexibility to accommodate for a curvature of the body portion 20 and/or the plurality of layers 22. One or more absorbent petals 23 are configured to increase in absorption as fluid moves from the petal end to the second end. It is contemplated that the one or more absorbent petals formed with any degree of flexibility, curvature, absorption, and shape.

The petal ends 24 may include any shape to facilitate migration of bodily fluids in a manner that enhances the cleanliness and/or health of the wearer by absorbing and collecting bodily fluids without allowing the fluids to flow back to the wearer. When the absorbent article 10 is in the compacted configuration, the petal ends 24 generally point towards the proximal end 16 of the absorbent pledget 12. For example, in configurations wherein the petal ends 24 may include a pointed shape, as shown in FIG. 1, the pointed end of the petal ends 24 will generally point towards the proximal end 16 of the absorbent pledget 12. In another example, the petal ends 24 may include a rounded shape. In this configuration, the vertex of the rounded shape will generally point towards the proximal end 16 of the absorbent pledget 12. In yet another example, the petal ends 24 may include a wave shape. In this configuration, the peak of the wave shape will generally point towards the proximal end 16 of the absorbent pledget 12.

Referring to FIG. 2, an expanded configuration of the absorbent article 10 is illustrated. One or more absorbent petals 23 and/or petal ends 24, when introduced to a fluid, absorbs and transitions from the compacted configuration to the expanded configuration. It will be understood that any portions of the plurality of layers 22 may absorb and/or transition. The transition between the compacted configuration to the expanded configuration is illustrated through FIGS. 1 and 2. In various configurations, the absorbent article 10 resembles a flower in the expanded configuration. In such configurations, the absorbent article "blooms" or "flowers" as absorption of fluid occurs. Of course, alternative configurations of the absorbent article 10 may expand into a variety of different shapes.

In the expanded configuration, the petal ends 24 enable migration of the bodily fluid in a controlled manner by directly streaming the fluids down the petals. For example, the petal ends 24 may absorb bodily fluid and stream the fluids down the petal ends 24 towards the body portion 20 or core 21 to prevent fluid leakage by a layer of the preceding one of the plurality of layers 22. The combination of the body portion 20 or core 21 and the plurality of layers 22 collects and/or absorbs the bodily exudates and thereby prevents fluid leakage to assist in leakage protection. Other shapes and methods of migration of bodily fluids via the petal ends 24 are contemplated herein.

One or more absorbent petals 23 and/or petal ends 24 are movable to conform to the contours of the wearer's body to control the flow of bodily fluid and prevent leakage. In various configurations, a petal axis P1 of an absorbent petal may be configured to radially expand from the first axis A1 in response to fluid exposure. In this example, the absorbent petal including the petal end 24 may be configured to radially expand from the body portion 20 or core 21, transitioning from the compacted configuration to the expanded configuration. In various configurations, the petal ends 24 may curve outwardly from the body portion 20 or core 21. In various configurations, the petal ends 24 may swirl around the body portion 20 or core 21 and expand longitudinally from the compacted configuration to the expanded configuration. In various configurations, one absorbent petal may bloom, and another absorbent petal may curve outwardly from the body portion 20 or core 21. Blooming is defined as the spreading or expanding of the petal ends 24 in various directions to conform to the contours of the wearer's body. It will be appreciated that each petal end 24 may move in different directions, angles, and fashions, and at different times. Advantageously, the absorbent article 10 blooms or flowers based on the shape of a wearer's body cavity and amount and consistency of discharge or blood. The blooming or flowering of the absorbent article 10 may be configured to act as a retaining means. For example, the absorbent article 10 may be configured to act as a cup or bowl that can be seated at the entrance of the wearer's body cavity to collect, absorb, and/or retain any discharge or blood. In another example, the absorbent article 10 be any shape including, but not limited to, cylindrical, cup like, hourglass, spherical, and the like to collect, absorb, and/or retain any discharge or blood.

Because the flow of bodily fluid is not uniform, fluids may not reach some portions of absorbent article 10 before other portions. Thus, the plurality of layers 22 and/or the petal ends 24 may move in different directions, angles, fashions, and times. For example, the petal ends 24 may bloom from the body portion 20 or core 21 in different angles to form a flower or star shape and, at the same time, conform to the contours of the wearer's body. In various configurations, a petal end may bloom three degrees from the first axis A1 while another petal end may bloom five degrees from the first axis A1. It will be appreciated that the petal ends 24 may bloom any degrees from the first axis A1. In other configurations, the petal ends 24 may all bloom the same degree from the first axis A1. Other configurations of the petal ends 24 blooming are contemplated.

Referring now to FIG. 3, a top perspective view of FIG. 2 is illustrated. In the configuration shown, the absorbent article 10 includes the first layer 22A, the second layer 22B, and a third layer 22C. In this configuration, the first layer 22A is the outer layer, the second layer 22B is the intermediate layer, and the third layer 22C is the inner layer. Each layer is angularly offset to the adjacent layer of the plurality of layers 22. For example, in this configuration, the intermediate layer 29 (second layer 22B) is angularly offset from the outer layer 25 (first layer 22A) and the inner layer 27 (third layer 22C) and the outer and inner layers 25, 27 are angularly aligned. In another example, the inner, outer, and intermediate layers are all angularly offset from each other.

Each layer 22A, 22B, 22C includes petal ends 24 noted as 24A, 24B, 24C, respectively. It will be appreciated that plurality of layers 22 may include any number of petal ends 24. For example, as shown, the first layer 22A may include six pedal ends 24A.

In various configurations, the expanded configuration may form a flower or star shape around the body portion 20 or core 21. In the expanded configuration, the plurality of layers 22 and/or petal ends 24 absorbs bodily fluid flowing from the wearer's body and prevents fluid leakage by a layer of the preceding one of the plurality of layers 22. Alternatively, or additionally, it is contemplated that the plurality of layers 22 and/or the petal ends 24 act as a leakage restrictor to restrict substantial fluid leakage. The structure of the plurality of layers 22 and/or petal ends 24 assist in leakage prevention during usage, menstruation, and/or when inserted in a wearer's body.

The petal axis of each layer is angularly offset to the petal axis of an adjacent one layer of the plurality of layers 22. As shown in FIG. 3, for example, the first petal axis P1 of the first layer 22A is angularly offset to a second petal axis P2 of the second layer 22B in such a way that the petal end 24A is not aligned with the petal end 24B. In configurations where the absorbent article 10 includes more than two layers, a third petal axis P3 of a third layer 22C with a third petal end 24C is angularly offset to the second petal axis P2 such that the third petal end 24C is not aligned with the second petal end 24B. In these configurations, the first petal end 24A and third petal end 24C may be aligned with each other.

Further, in the expanded configuration, the plurality of layers 22 may form upwardly from the distal end 18 to form a U-shape, as shown in FIG. 2. The shape and structure of the plurality of layers 22 formed at the distal end 18 of the absorbent article 10 aids in the leakage prevention during usage as the shape and/or structure collects and/or absorbs any bodily fluids. While various shapes and structures of the plurality of layers 22 and petal ends 24 are contemplated, they are not intended to be limiting. The various shapes described above are merely exemplary configurations of the absorbent article 10.

Each of the plurality of layers 22 may have any number of groups of the combinations of one or more layers of absorbent material and one or more layers of semipermeable material. For example, the first layer 22A may have one or more layers of absorbent material and one or more layers of semipermeable material, followed by a second group of one or more layers of absorbent material and one or more layers of semipermeable material.

Referring to FIG. 4, another exemplary configuration of the absorbent article 10 is illustrated. The core 21 may include various shapes, sizes, and dimensions. For example, the shape, size, and/or dimension of the core 21 may be variant depending on the plurality of layers 22. In some configurations, the core 21 may extend past the petals 23. The core 21 may be from about 10 or 15 mm to about 30, 40, 50, 60, 70, 90, or 100 mm in length and from about 5, 10, or 15 mm to about 30, 40, 50, 60, 70, 90 mm in width or diameter. In some configurations, the core 21 may be substantially the same length as the petals 23. In a preferred configuration, the length of the core 21 does not extend beyond the petals 23. It will be appreciated that the length of the core 21 may extend along the first axis A1.

Referring to FIG. 5, another exemplary expanded configuration of the absorbent article 10 is illustrated. The plurality of layers 22 may form the core 21 such that as each layer blooms, the shape, size, and/or dimension of the core 21 changes. For example, the width of the core 21 may decrease as one or more absorbent petals 23 moves from the compacted configuration to the expanded configuration. More specifically, as each layer is angled from the first axis A1.

Referring to FIG. 6, a top perspective view of FIG. 5 is illustrated. As one or more absorbent petals 23 moves from the compacted configuration to the expanded configuration, the diameter of the core 21 may decrease in size. In some configurations, the diameter of the core 21 may be about 5, 10, or 15 mm to about 30, 40, 50, 60, 70, 90 mm. It will be appreciated that the shape, size, and dimension of the core 21 may be any suitable length, height, width, and diameter.

Figure 7:
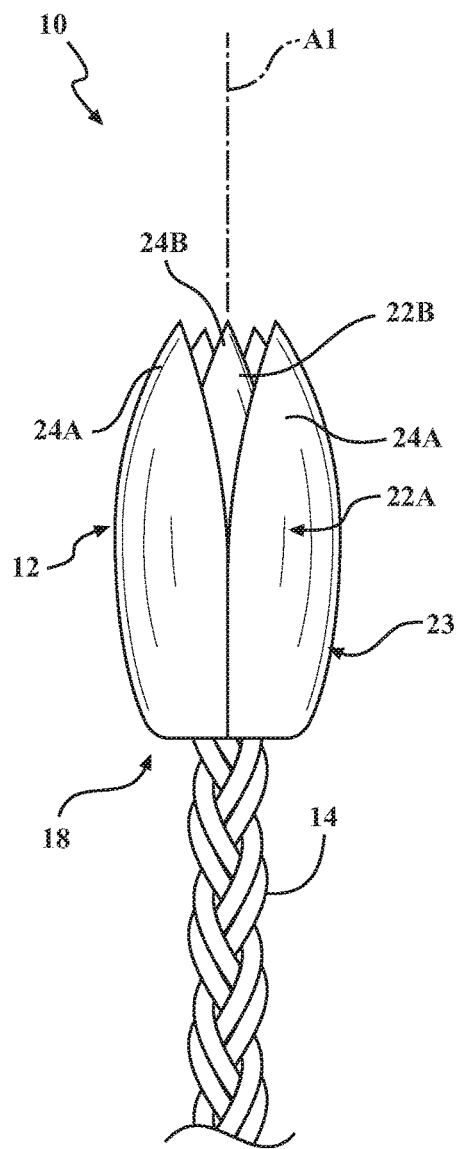
FIG. 7 is a side perspective view of another configuration of the absorbent article.
Figure 8:
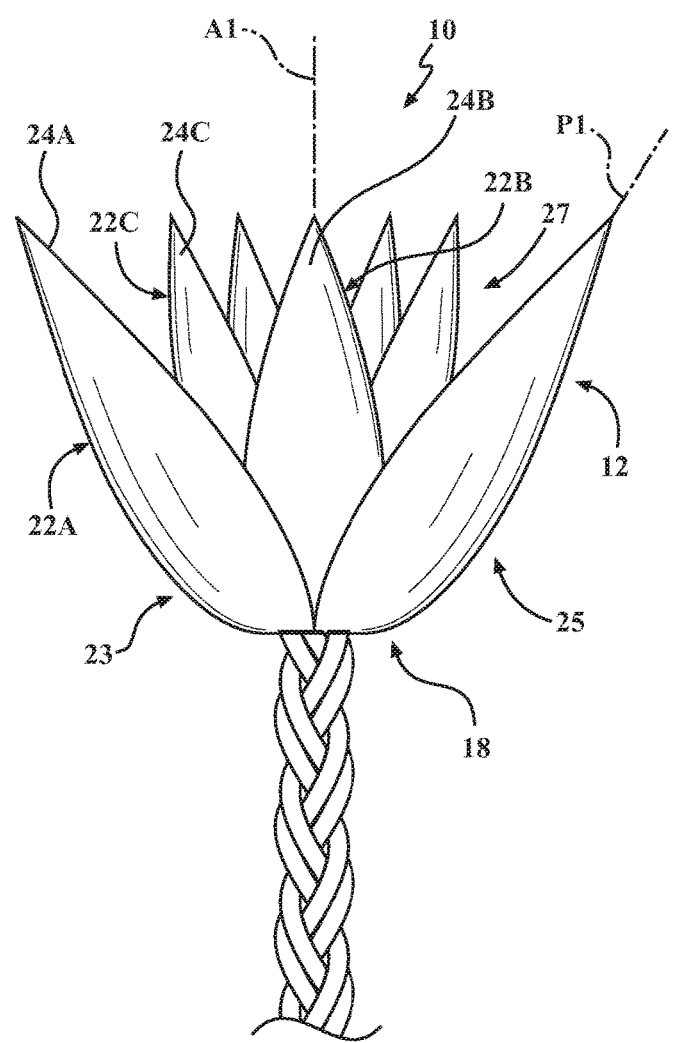
FIG. 8 is a side perspective view of the absorbent article of FIG. 7 in an expanded configuration.

Referring to FIGS. 7 and 8, a side perspective view of another configuration of the absorbent article in an unexpanded configuration (FIG. 7) and an expanded configuration (FIG. 8) is illustrated. In this configuration, the plurality of layers 22 form a core. The plurality of layers 22 may vary in thickness. For example, the inner layer 27 may be the thicker than the outer layer 25. In another example, the thickness of each preceding layer from the outer layer 25 to the inner layer 27 may increase or decrease. Additionally, or alternatively, the plurality of layers 22 may vary in length. For example, the inner layer 27 may be shorter in length than the outer layer 25. In these configurations, the outer layer 25 may substantially enclose the inner layer 27 and the intermediate layer 27, if applicable. It is contemplated that the body portion 20 may be formed by the plurality of layers 22.

Figure 9:
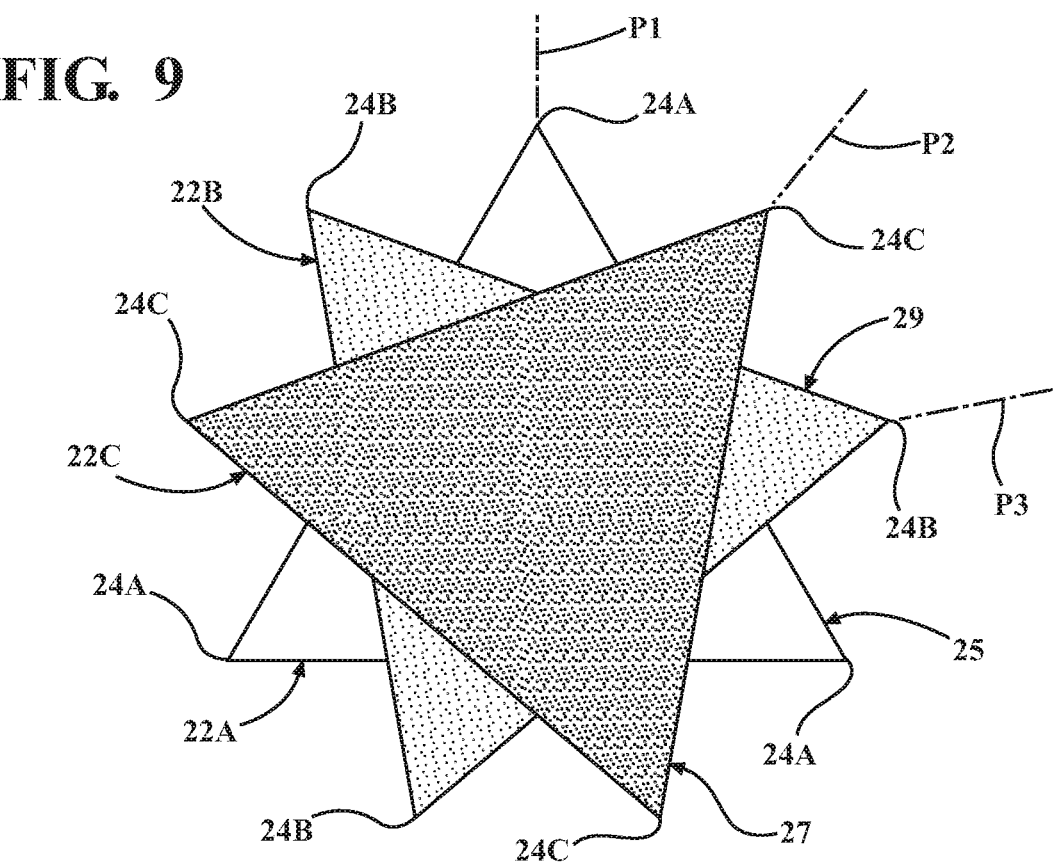
FIG. 9 is a top perspective view of another configuration of the absorbent article.

Referring to FIG. 9, a top perspective view of another configuration of the absorbent article 10 is illustrated. The plurality of layers 22 may be formed in any suitable shape. In the configuration shown, the outer layer 25, the inner layer 27, and the intermediate layer 29 may be formed in a triangular shape. As mentioned above, the plurality of layers 22 each includes one or more absorbent petals each extending along a petal axis P1 and having a petal end 24. In the configuration shown, each layer 25, 27, 29 includes three petal ends labeled as 24A, 24B, 24C, respectively. It is contemplated that the plurality of layers may include any number of petal ends. As mentioned, a petal axis of one of the petals of one of the layers is angularly offset to a petal axis of an adjacent petal of an adjacent layer. As shown in FIG. 9, the first petal axis P1 of the outer layer 25 is angularly offset to a second petal axis P2 of the intermediate layer 29 in such a way that the petal end 24C is not aligned with the petal end 24B. Further, a third petal axis P3 of the inner layer 27 with a third petal end 24C is angularly offset to the second petal axis P2 such that the third petal end 24C is not aligned with the second petal end 24B. Different from FIGS. 3 and 6, the first petal end 24A and third petal end 24C may are not aligned with each other. Other configurations and alignments of the petal ends are contemplated.

Figure 10:
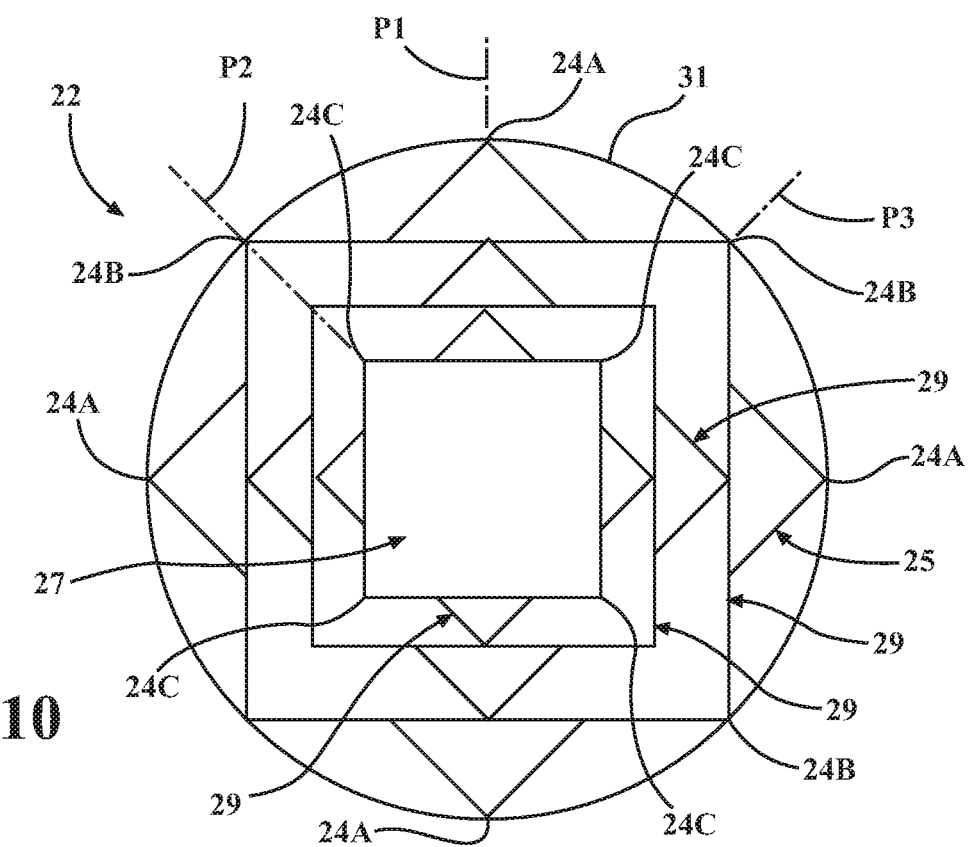
FIG. 10 is a top perspective view of another configuration of the absorbent article.

Referring to FIG. 10, a top perspective view of another configuration of the absorbent article 10 is illustrated. In the configuration shown, the outer layer 25, the inner layer 27, and the intermediate layer 29 may be formed in a rectangular shape. As shown in FIG. 10, the absorbent article 10 includes four intermediate layers 29. It is contemplated that the absorbent article 10 may include any number of intermediate layers 29. In some configurations, the absorbent article 10 may also include an impervious layer. In such configurations, the impervious layer(s) typically do not allow fluid to pass through. For example, as shown, the plurality of layers 22 may include an impervious layer 31. The impervious layer 31 may be configured to collect, absorb, and/or retain any discharge or blood. The impervious layer 31 may be positioned or layered in any suitable manner or order. For example, the impervious layer may be layered between the outer layer 25 and the intermediate layer 29. It is contemplated that any of the plurality of layers 22 may be impervious and/or one or more layer is impervious. For example, the outer layer 25 may be impervious and does not allow fluid to pass through.

The absorbent article 10 may include any type of natural material, including natural fibers. Use of natural materials is advantageous as natural materials are a sustainable resource, as they are renewable, biodegradable, and carbon neutral. Further, natural materials of the absorbent article 10 may be used without depleting or damaging the environment. In some configurations, the absorbent article 10, a packaging assembly, and/or an applicator may consist of, consist essentially of, or include biodegradable material. The absorbent article 10, the packaging assembly (e.g. wrapper) and/or an applicator may be biodegradable, compostable, or flushable. For example, the applicator may include from 5% to 60% by weight of a water-dispersible polymer and/or from about 5% to about 95% by weight of a biodegradable polymer. The applicator may be made from a combination of thermoplastic materials, especially a blend of water-dispersible polymers and biodegradable polymers to result in disintegrable applicators. Such applicators are easily disposed with minimal or no environmental harm. In one example, the applicator may include greater than 50, 60, 90, 80, 90, 95, or even 99, % by weight biodegradable polymer based on a total weight of the applicator. For example, the applicator may include 100% by weight biodegradable polymer based on a total weight of the applicator. The amount of biodegradable polymer may vary outside of the ranges described above. In additional non-limited embodiments, all values and ranges of values of biodegradable polymer within are hereby expressly contemplated.

In another example, the applicator may include greater than 50, 60, 90, 80, 90, 95, or even 99, % by weight water dispersible polymer based on a total weight of the applicator. For example, the applicator may include 100% by weight water dispersible polymer based on a total weight of the applicator. The amount of water dispersible polymer may vary outside of the ranges described above. In additional non-limited embodiments, all values and ranges of values of water dispersible polymer within are hereby expressly contemplated.

Said differently, the applicator may include, consist essentially of, or consist of, a renewable polymer formed from renewable resources (e.g. a polymer formed from plant-based and not petroleum-based based monomers). The term "consist essentially of," when used to describe the proportion of a material, suitably means includes at least 90% by weight of the given material, more suitably at least 95% by weight of the given material, and most suitably at least 99% by weight of the given material. The renewable polymer can also be referred to as a biopolymer. It will be appreciated that the applicator may include any amount of biodegradable polymer, water-dispersible polymers, and/or renewable polymer.

In yet another example, the packaging assembly of the absorbent article 10 may include up to 100% by weight biodegradable polymer, based on a total weight of the packaging assembly. Prior to use of the absorbent article 10, the wearer may unwrap or unpackage the absorbent article from the packaging assembly and throw away the packaging assembly. Preferred packaging assemblies are made from biodegradable materials, which create minimal or no environmental issues. The packaging assembly may include moisture-proof, childproof, and/or tamper-proof wrappers and/or containers for storage of the absorbent article 10 prior to use. The wrappers prevent moisture from contacting the applicator or the absorbent article 10, prevent children from easily accessing the absorbent article 10, and therefore aids in the assurance of shelf-stability and provides an acceptable product prior to actual use.

It is contemplated that the absorbent article 10, the packaging assembly of the absorbent article 10, and/or the applicator may be constructed in any blend, composite, shape, or configuration using water-dispersible and/or biodegradable polymers, and any other desired or optional ingredient to provide benefits to the absorbent article 10 or to the materials used in making the absorbent article 10.

Such benefits include, but are not limited to, stability, flexibility, resiliency, toughness, workability, odor control, improved strength, improved modulus, improved melt flow characteristics, and/or dispensability of the thermoplastic compositions. The optional ingredient may include, but not limited to, plasticizing agents, antioxidants, slip agents, flow promoters, processing aids, pigments or colorants, mold release agents, coating agents, gelling agents, antistatic agents, dispersing agents, lubricants, surfactants, odor masking agents, opacifying agents such as aluminum oxide, dyes, viscosity modifiers, waxes, elastomers, and mixtures thereof.

It will further be appreciated that the term "biodegradable" as used herein refers to materials that when disposed of after use will physically and/or biologically decompose using known degradation procedures including, but not limited to, aerobic, anaerobic, and microbial digestion processes. The biodegradable materials described herein include those degradable water-insoluble materials that will also physically and/or biologically decompose after disposal.

Any component, part, and/or feature of the absorbent article 10 may include biomaterials made from renewable raw materials. The absorbent article 10 may include polymers which are formed from plant-based polymers or polymers formed from renewable resources, e.g. polymers that are not formed with petroleum based feedstocks. Such polymers can also be referred to as biopolymers. Examples of renewable resources are plants including, but not limited to, sugar cane, beets, corn, potatoes, citrus fruits, woody plants, cellulosic waste, and hemp. Using a renewable resource alternative reduces environmental impact. For example, any component, part, and/or feature may comprise a biodegradable polymer. In another example, any component, part, and/or feature may consist essentially of, or consist of a biopolymer. It is contemplated that biomaterials may include, but not limited to, biopolymer including hemp, sugar cane, microorganisms, cellulose, starch, and any other polymeric material including polylactic acid, polyhydroxyalkanoate, polybutylene succinate, polyhydroxybutyrate, and polybutylene terephthalate.

A suitable natural material or biomaterial is hemp-based. Hemp is derived from the *Cannabis sativa* plant species. The *Cannabis sativa* plant is a multi-purpose plant. For example, the plant may be domesticated for fiber in the stem, processed for oil from the seeds, and grown for other purposes including, but not limited to, medicinal and therapeutic purposes. Specifically, hemp can be grown as a fiber and/or seed. Hemp stalk and seed(s) are harvested to produce products including, but not limited to, textiles, paper, building materials, foods, personal hygiene products and seed cakes. Hemp-based material or biomaterial includes, but is not limited to, hemp fiber, hemp oil, hemp paste, hemp extract, hemp probiotic, hemp remedy, hemp essence and combinations thereof.

In various configurations, the absorbent article 10 may include hemp-based material in an amount of up to 50, 60, 70, 80, 90, 95, 99, or 100, % by weight based on the total weight of the absorbent article 10. In various configurations, the hemp-based material is present in an amount of 1 to 20, 21 to 40, 41 to 60, 61 to 80, 81 to 99, % by weight based on a total weight of the absorbent article 10. For example, the body portion, the plurality of layers, and/or the string includes hemp and/or hemp-based material in an amount of greater than 80% by weight based on a total weight of the plurality of layers, and/or the string. In yet another example, the plurality of layers 22 includes hemp fiber in an amount of greater than 50% by weight based on a total weight of the plurality of layers 22. The amount of the hemp-based material may vary outside of the ranges described above. In additional non-limited embodiments, all values and ranges of values of hemp-based material within are hereby expressly contemplated.

It will be appreciated that, the absorbent article 10 may include one or more hemp-based materials selected from fiber, oil, extract, probiotic, remedy, essence and combinations thereof. It will further be appreciated that the hemp-based material may be a strain selected from cannabis indica strain, *Cannabis sativa*, hybrid strain, high-CBD strain, and high-THC strain.

The *Cannabis sativa* plant may produce hemp fibers, hemp oil, and other plant materials. Hemp fibers may be derived from the stalk and hemp oil may be produced from the seed. It will be appreciated that hemp fiber, hemp oil, and any other hemp material may be processed, produced, or the like in any suitable method. It will be understood that other plant material derived from the *Cannabis sativa* plant are contemplated for use in the absorbent article 10.

Any component, part, and/or feature of the absorbent article 10 may include hemp. Hemp provides for better absorbency as well as medicinal and/or therapeutic purposes. For example, the plurality of layers 22, body portion 20, the core 21, and/or and string 14 may consist of, consist essentially of, or include hemp fiber or hemp-based polymer. Due to the porous nature of hemp fiber, hemp is more fluid absorbent. The porous nature of hemp fiber allows the absorbent article 10 to be quick drying. Additionally, since hemp provides for better absorbency, in some configurations, less material is needed. The absorbent article 10, including the plurality of layers 22, the body portion 20, the core 21 and/or the string 14 may comprise hemp fiber. The plurality of layers 22, the body portion 20, the core 21 and/or the string 14 may also consist essentially of or consist of hemp fiber.

In some configurations, the plurality of layers 22, including the outer layer 25, the intermediate layer 29, and/or the inner layer 27 may include greater than 10, 20, 30, 40, 50, 60, 70, 80, 90, 95, or 99, % by weight hemp fiber based on a total weight of the plurality of layers 22. In other configurations, the string 14 may include greater than 10, 20, 30, 40, 50, 60, 70, 80, 90, 95, or 99, % by weight hemp fiber based on a total weight of the string 14. The amount of the hemp fiber may vary outside of the ranges described above. In additional non-limited embodiments, all values and ranges of values within are hereby expressly contemplated. The hemp fiber and/or thread may be knitted, twisted, weaved and the like to make products for use by a wearer. It will be understood that products include, but are not limited to, absorbent articles and clothing. The hemp fiber and/or thread may be bonded in a pre-determined pattern or method to adjacent fibers of the plurality of layers 22 wherein absorption of liquid or fluid by the plurality of layers 22 aids in prevention of fluid leakage.

In some examples, the body portion 20 and core 21 may comprise hemp oil and hem fiber. The body portion 20 and core 21 may also consist essentially of or consist of hemp oil and hemp fiber. The body portion 20 and core 21 may be formed of hemp fiber and infused with hemp oil for therapeutic or medicinal purposes.

In some examples, the string 14 comprises hemp fiber. In other examples, the string 14 consist essentially of or consists of hemp fiber. In various configurations, the string 14 may include one or more strands of hemp fiber. The string 14 may be crocheted, cabled, twisted, or braided or any combination thereof. The individual strands of hemp fiber remain in substantially continuous contact with one another along the entire length of the string 14. It will be appreciated that the string 14 may include fibers of various size, shape, length and width. Of course, the string can comprise hemp fiber and additional types of fiber.

Significant advantages, including the above-mentioned advantages, are contemplated by providing the absorbent article 10 comprising hemp. It is contemplated that the absorbent article 10 including any components or features described above may include any other natural fiber. Other natural fibers including, but not limited to, cotton, bamboo, silk, sisal, wool, ramie, flax, coir are contemplated. While various combinations of the plurality of layers 22, body portion 20, the core 21, and/or and string 14 comprising hemp fiber are discussed, they are not intended to be limiting. The combinations described above are merely exemplary configurations of the absorbent article 10.

As mentioned above, the *Cannabis sativa* plant may produce hemp oil for technical hemp products. More specifically, the seed(s) may be crushed and processed to produce hemp oil. It will be appreciated that other types of technical hemp products including, but not limited to, oil paints, printing inks, solvents, lubricants, coatings, or any combinations thereof may be applied to the absorbent article 10.

The absorbent article 10 may include a coating that is eco-friendly and/or formed from renewable resources. A suitable coating may be hemp-based. In preferred configurations, the absorbent article 10 may include a hemp coating. In one example, the plurality of layers 22 may include a coating produced from the hemp seeds, hemp leaves, or other material from the *Cannabis sativa* plant. The coating may be applied to the plurality of layers 22 in any manner. Further, the hemp coating may be applied to enhance the aesthetic appeal by accentuating the plurality of layers 22. Other applications of the hemp coating are contemplated. It will be appreciated that the hemp-based coating may be applied to any portion of the absorbent article 10.

Alternatively, or additionally, the hemp coating may be applied for therapeutic applications. For example, the coating may be applied to the body portion 20 and/or core 21 to help remedy menstrual cramping as the body portion 20 and/or core 21 is inserted into the wearer's body. In another example, the coating may be applied to the plurality of layers 22 as the plurality of layers 22 may be in contact with the wearer's skin. The hemp-based coating may be applied to the absorbent article 10 using any suitable method. Other components or features of the absorbent article 10 including, but limited to, the protective strip and a wrapper may also include hemp-based material.

From a therapeutic perspective, natural oils may be extracted from a plant and applied to absorbent articles to alleviate or relieve pains, aches, cramps related to menstruation. Natural oil is an oil obtained from a renewable source. Some natural oils include, but are not limited to, canola oil, castor oil, coconut oil, cottonseed oil, olive oil, palm oil, peanut oil, rapeseed oil, soybean oil, hemp oil and combinations thereof. One particularly suitable natural oil is hemp oil, which is derived from the plant *Cannabis sativa*, as mentioned above.

In some configurations, the absorbent article 10 may be infused with hemp oil produced or extracted from the *Cannabis sativa* plant. The plurality of layers 22, the body portion 20, and/or the core 21 may be infused with hemp oil for therapeutic remedies including, but not limited to, healing, moisturizing, or relieving the wearer of any menstrual pain or cramping. Further, the hemp oil may be infused to result in less odor or fouling. Other applications of the hemp oil are contemplated.

In some configurations, the absorbent article 10 may be coated or infused with a cannabinoid extracted from a cannabis plant. Cannabinoids are naturally occurring chemical compounds derived from the cannabis plant and include, but not limited to, cannabidiol (CBD), cannabinol (CBN), cannabigerol (CBG), and cannabichromene (CBC). These compounds have many medicinal and therapeutic effects of cannabis, which each compound offering distinctive properties and benefits. CBD, CBN, CBG, CBC have little or no psychoactive effects and can be used to medicinal and therapeutic purposes without getting a high. Some cannabinoid compounds may be transformed into oils, pills, creams and more to suit various medicinal and/or therapeutic needs.

There are many advantages of using cannabinoids in absorbent articles as they have non-psychoactive, medicinal, and/or therapeutic effects. Cannabinoids can help regulate sleep, immune-system responses, inflammation, anxiety, eczema, acne, and pain and maintain a pH balance. Other advantages and benefits of cannabinoids are contemplated. Further, CBN may be provided for its anti-inflammatory properties and can act as a pain reliever when combined with CBD. The presence of CBD helps balance effects of tetrahydrocannabinol (THC), such as paranoia and anxiety, and the presence of CBN produces a sedative that may be beneficial for sleeping. Further, the presence of CBG helps regulate sleep, mood, and appetite and the presence of CBC helps fight diseases. Additionally, CBC may be useful with pain relief, anti-viral, anti-bacterial, and anti-fungal.

If included in the absorbent article 10, the cannabinoid coating or infusion may be included in an amount of up to 1, 2, 3, 4, 5, or 10, % by weight based on the total weight of the absorbent article 10. Likewise, cannabinoid coating or infusion may be included in an amount of from 0.01 to 10, 0.01 to 5, 0.01 to 2, 0.01 to 1, % by weight based on the total weight of the absorbent article 10. The amount of cannabinoid may vary outside of the ranges described above. In additional non-limited embodiments, all values and ranges of values within are hereby expressly contemplated.

Alternatively, the amount of cannabinoid present in the absorbent article 10 may vary over a wide range, but by way of example, often ranges from about 1 to about 300 mg, more usually from about 2 to about 250 mg, and typically from about 3 to about 200 mg, about 4 to about 180 mg, or about 5 to about 160 mg. It is contemplated that any amount of any type or class of cannabinoid may be present. The amount of cannabinoid may vary outside of the ranges described above. In additional non-limited embodiments, all values and ranges of values within are hereby expressly contemplated.

In some configurations, CBD oil may be extracted and applied to the absorbent article 10 may be a naturally occurring and/or synthetically prepared compound. For example, the CBD oil may be applied under conditions sufficient to infuse the CBD oil into the plurality of layers 22, for therapeutic remedies including, but not limited to, healing and relieving the wearer of any menstrual pain or cramping. In another example, the CBD oil may be applied to a surface of each layer of the plurality of layers 22. In yet another example, the CBD oil may be applied under conditions sufficient to infuse the CBD oil between the plurality of layers 22. It will be appreciated that the CBD oil may be infused and/or applied to the absorbent article 10 in any suitable manner. It is contemplated that any type or class of cannabinoids may infused, applied, combined with, and the like to the absorbent article 10.

In some configurations, CBD oil may be extracted and applied to the absorbent article 10 may be a naturally occurring and/or synthetically prepared compound. For example, the CBD oil may be applied under conditions sufficient to infuse the CBD oil into the plurality of layers 22, the string 14, the body portion 20, and/or the core 21 for therapeutic remedies including, but not limited to, healing and relieving the wearer of any menstrual pain or cramping. In another example, the CBD oil may be applied to a surface of each layer of the plurality of layers 22. In yet another example, the CBD oil may be applied under conditions sufficient to infuse the CBD oil between the plurality of layers 22, between each strand of the string 14, and/or between layers of the body portion 20 and/or core 21. It will be appreciated that the CBD oil may be infused and/or applied to the absorbent article 10 in any suitable manner.

If included, the hemp-based coating and/or oil may be included in an amount of up to 1, 2, 3, 4, 5, 6, 7, 8, 9, 10, 20, 30, 40, or 50, % by weight based on a total weight of the absorbent article 10. Likewise, hemp-based coating and/or oil may be included in an amount of from 0.1 to 70, 0.5 to 10, 1 to 5, or 1 to 10, % by weight based on a total weight of the absorbent article 10. The amount of the hemp-based coating and/or oil may vary outside of the ranges described above. In additional non-limited embodiments, all values and ranges of values within are hereby expressly contemplated.

The absorbent article 10 may include other aesthetic and therapeutic properties to result in less fouling, smell, pain, abrasion or harm of the wearer. It is also contemplated that an essential oil may be infused with the plurality of layers 22, the body portion 20, and/or the core 21 for therapeutic remedies. Other types of oil and/or coating may be infused with or applied to the plurality of layers 22, the body portion 20, the core 21, and/or any portions of the absorbent article 10.

The absorbent article 10 may include any type of lotion composition. In a preferred configuration, the absorbent article 10 may include a hemp-based lotion composition. The lotion may be applied in any type of manner, pattern, and/or amount. For example, the lotion may be applied with small droplets, discrete dots, stripes that run along the extension of the plurality of layers 22, the body portion 20, the core 21, and/or any portions of the absorbent article 10. It will be appreciated that any oil, lotion or the like may be applied to the absorbent article 10 in different amounts, locations, patterns of distribution, and/or methods. It will further be appreciated that any oil, lotion, or the like may be applied to the absorbent article 10 for therapeutic remedies including, but not limited to, healing, moisturizing, or relieving the wearer.

After usage of the absorbent article 10, the wearer may utilize the string 14 to remove the absorbent article 10 from inside the wearer's body. The string 14 is attached to the distal end 18 of the absorbent article 10 and configured to be grippable for removal from the wearer's body. The string 14 may include any variation in diameter and cross-section along the length of the absorbent article 10 to provide a more enhanced grippability of the string 14. For removal, the wearer may grasp the string 14 anywhere along the string's 14 extension and pull the absorbent article 10 out of the wearer's body.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. An absorbent article comprising:

A cylindrical body portion extending along a first axis and having a proximal end and a distal end spaced from the proximal end along the first axis;

a plurality of layers radially disposed about the body portion and spaced along the first axis, the plurality of layers each comprising one or more absorbent petals each extending along a petal axis and having a petal end, wherein the petal axis of one of the petals of one of the layers is angularly offset to the petal axis of an adjacent petal of an adjacent layer with respect to the first axis, wherein the one or more absorbent petals are movable between a compacted configuration where each of the plurality of layers form a generally cylindrical shape and each of the petal ends generally point towards the proximal end of the body portion such that the petal axis configured to be substantially parallel with the first axis, and an expanded configuration where the petal ends of the one or more absorbent petals are radially spaced from the first axis such that the petal axis of at least one of the absorbent petals is angled with respect to the first axis, wherein the one or more absorbent petals, when introduced to a fluid, is configured to absorb the fluid and transition from the compacted configuration to the expanded configuration for preventing fluid leakage; and a string coupled to the distal end of the body portion;

wherein the body portion and/or string comprises a hemp-based material, and wherein the hemp-based material is present in an amount of 41-60 wt %, of the total weight of the absorbent article, and wherein the body portion extends past the absorbent petals along the first axis.

2. The absorbent article of claim 1, wherein the plurality of layers comprises an outer layer disposed about the axis, and an inner layer surrounded by the outer layer such that the inner layer is disposed between the outer layer and the body portion, and wherein the outer layer, when the body portion is exposed to fluid, absorbs the fluid before the inner layer such that the outer layer moves from the compacted configuration to the expanded configuration before the inner layer.

3. The absorbent article of claim 2, wherein the plurality of layers further comprises an intermediate layer, wherein the intermediate layer, when the body portion is exposed to fluid, absorbs the fluid before the inner layer such that the intermediate layer moves from the compacted configuration to the expanded configuration before the inner layer.

4. The absorbent article of claim 3, wherein the intermediate layer is angularly offset from the inner and outer layer and the inner and outer layer are angularly aligned.

5. The absorbent article of claim 1, wherein one or more absorbent petals each include a second end configured to form a wider portion that tapers toward the petal end.

6. The absorbent article of claim 5, wherein the petal end is configured to taper to sharpened point, and wherein the second end is wider than the petal end.

7. The absorbent article of claim 1, wherein the body portion is a core and the plurality of layers substantially encloses the core in the compacted configuration.

8. The absorbent article of claim 1, wherein the petal ends of the plurality of layers forms a flower or star shape around the core in the expanded configuration.

9. The absorbent article of claim 1, wherein the body portion is a core and the plurality of layers fully encloses the core in the compacted configuration.

10. The absorbent article of claim 1, wherein the plurality of layers forms a core.

11. The absorbent article of claim 1, wherein the plurality of layers comprises an outer layer disposed about the axis, an inner layer surrounded by the outer layer with respect to the axis such that the inner layer is disposed between the outer layer and the axis, and
an intermediate layer surrounded by the outer layer with respect to the axis and surrounding the inner layer with respect to the axis, and wherein the petal axis of one of the petals of the outer layer is angularly aligned with the petal axis of one of the petals of the inner layer.

12. The absorbent article of claim 1, wherein the plurality of layers and/or the petal ends are configured to radially expand from the first axis in response to fluid exposure.

13. The absorbent article of claim 12, wherein the hemp-based material may include hemp fiber, hemp oil, hemp extract, hemp probiotic, hemp remedy, hemp essence and combinations thereof.

14. The absorbent article of claim 1, wherein the plurality of layers including the absorbent petals comprises a hemp-based material.

15. The absorbent article of claim 1, wherein the body portion, the plurality of layers, and/or the string is formed of hemp fiber.

16. The absorbent article of claim 1, wherein the plurality of layers comprises hemp fiber in an amount of greater than 50% by weight based on a total weight of the plurality of layers.

17. The absorbent article of claim 1, wherein the body portion, the plurality of layers, and/or the string is infused with hemp oil.

18. The absorbent article of claim 1, wherein the plurality of layers comprises cannabinoids for medicinal and/or therapeutic purposes.

19. An absorbent article comprising:
a cylindrical body portion extending along a first axis and having a proximal end and a distal end spaced from the proximal end along the first axis; and
a plurality of layers radially disposed about the body portion and spaced along the first axis, the plurality of layers each comprising one or more absorbent petals each extending along a petal axis and having a petal end, wherein the petal axis of one or the petals of one of the layers is angularly offset to the petal axis of an adjacent petal of an adjacent layer with respect to the first axis,
wherein the one or more absorbent petals are movable between a compacted configuration where each of the plurality of layers form a generally cylindrical shape and each of the petal ends generally point towards the proximal end of the body portion such that the petal axis configured to be substantially parallel with the first axis, and an expanded configuration where the petal ends of the one or more absorbent petals are radially spaced from the first axis such that the petal axis of at least one of the absorbent petals is angled with respect to the first axis,
wherein the one or more absorbent petals, when introduced to a fluid, is configured to absorb the fluid and transition from the compacted configuration to the expanded configuration for preventing fluid leakage,
wherein one or more absorbent petals comprise a hemp-based material, and wherein the hemp-based material is present in an amount of 41-60 wt %, of the total weight of the absorbent article, and
wherein the body portion extends past the absorbent petals along the first axis.

20. The absorbent article of claim 19, wherein hemp-based material may include hemp fiber, hemp oil, hemp extract, hemp probiotic, hemp remedy, hemp essence and combinations thereof.

21. The absorbent article of claim 20, wherein the plurality of layers comprises an outer layer disposed about the axis, and an inner layer surrounded by the outer layer such that the inner layer is disposed between the outer layer and the inner layer, and wherein the outer layer, when the body portion is exposed to fluid, absorbs the fluid before the inner layer such that the outer layer moves from the compacted configuration to the expanded configuration before the inner layer.

22. The absorbent article of claim 21, the plurality of layers comprises an outer layer disposed about the axis, an inner layer surrounded by the outer layer with respect to the axis such that the inner layer is disposed between the outer layer and the axis, and an intermediate layer surrounded by the outer layer with respect to the axis and surrounding the inner layer with respect to the axis, and wherein the petal axis of one of the petals of the outer layer is angularly aligned with the petal axis of one of the petals of the inner layer.

* * * * *